US00PP09959P

United States Patent [19]

Bradford et al.

[11] Patent Number: Plant 9,959

[45] Date of Patent: Jul. 15, 1997

[54] NECTARINE TREE "RUBY PEARL"

[76] Inventors: Lowell Glen Bradford, 12439 E. Savana Rd.; Norman G. Bradford, 11875 E. Savana Rd., both of Le Grand, Calif. 95333

[21] Appl. No.: 638,834

[22] Filed: Apr. 29, 1996

[51] Int. Cl.[6] ..... A01H 5/00

[52] U.S. Cl. ..... Plt./40.1

[58] Field of Search ..... Plt./40.1, 41.1

[56] References Cited

U.S. PATENT DOCUMENTS

P.P. 3,165 5/1972 Anderson ..... Plt./41.1
P.P. 9,360 11/1995 Bradford et al. ..... Plt./40.1

*Primary Examiner*—James R. Feyrer

[57] ABSTRACT

The present invention relates to a nectarine, *Prunus persica*, tree and more particularly to a new and distinct variety broadly characterized by a medium size, medium vigorous, productive and regular bearing tree. The fruit matures under the ecological conditions described approximately the last week in June, with first picking on Jun. 26, 1995. The fruit is uniformly medium in size, subacidic in flavor, globose in shape, clingstone in type, very firm in texture, and nearly full red in skin color. The variety was a first generation cross using Red Diamond (U.S. Plant Pat. No. 3,165) yellow flesh nectarine as the selected seed parent and June Pearl (U.S. Plant Pat. No. 9,360) white flesh nectarine as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as "Ruby Pearl". The present variety was developed by us in 1992 in a cultivated area of our experimental orchard at Bradford Farms near Le Grand, Calif. in Merced County (San Joaquin Valley). It was a first generation cross using Red Diamond (U.S. Plant Pat. No. 3,165) yellow flesh nectarine as the seed parent and June Pearl (U.S. Plant Pat. No. 9,360) white flesh nectarine as the selected pollen parent. Subsequent to origination of the present variety of nectarine tree, we asexually reproduced it by budding and grafting, and such reproduction of plant and fruit characteristics were true to the original plant in all respects.

The fruit produced by the presen variety is most similar to its pollen parent, the June Pearl (U.S. Plant Pat. No. 9,360), by producing white flesh clingstone nectarines that are subacidic in flavor, medium in size, full red in skin color and virtually free from red texture bleeding, but is distinguished therefrom and an improvement thereon by producing fruit that ripens about two weeks later, that is firmer in texture, that is sweeter in flavor, and that is less prone to protruding at the apex.

The present variety is similar to its seed parent, Red Diamond (U.S. Plant Pat. No. 3,165) by producing very firm, full red nectarines that ripen the last week in June, but is very distinguished therefrom by producing fruit that is white flesh instead of yellow flesh, that is clingstone instead of freestone, and that is subacidic in flavor instead of acidic.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Jul. 3, 1995. All major color code designatoins are by reference to the Inter-Society Color Council, National Bureau of Standards. Common color names are also used occasionally.

Tree

Size: Medium.
Vigor: Medium.
Growth: Upright and dense.
Form: Vase formed.
Hardiness: Hardy.
Production: Productive.
Bearing: Regular bearer.
Trunk:
- *Size.*—Medium.
- *Texture.*—Medium.
- *Bark color.*—Grayish brown [61. gy.Br].
- *Lenticels.*—Numerous. Color: Brownish orange [54. brO]. Average size: ⅛" to ⅜" [3.2–9.5 mm.].

Branches:
- *Size.*—Medium.
- *Texture.*—Medium.
- *Color.*—1st year wood topside: Light grayish red [18. l.gy.R]. 1st year wood underside: Brilliant yellow green [116. brill.YG]. Older wood: Deep yellowish brown [75. deep yBr].
- *Lenticels.*—Numerous, small. Color: Dark orange yellow [72. d.OY]. Average size: 1/32" to 1/16" [0.8–1.6 mm.].

Leaves:
- *Size.*—Medium. Average length: 5½" [139.7 mm.]. Average width: 1⅝" [41.3 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Moderate olive green [125. m.OlG]. Ventral surface: Moderate yellow green [120. m.YG].

*Margin.*—Finely serrate.
*Venation:*—Pinnately net veined.
*Petiole.*—Average length: 5/8" [15.9 mm.]. Average thickness: 1/16" [1.6 mm.]. Color: Strong yellow green [117. s.YG].
*Stipules.*—Numerous. Average length: 3/8" [9.5 mm.].
*Glands.*—Numbers: 2 to 6 per leaf. Position: Some oppositely and some alternately positioned on petiole and base of blade. Size: Medium. Form: Reniform. Color: Brilliant yellow green [116. brill.YG].

Flower buds:
*Hardiness.*—Hardy.
*Size.*—Medium.
*Length.*—Medium.
*Form.*—Free.
*Surface.*—Pubescent.

Flowers:
*Blooming period.*—Medium as compared with other varieties.
*Size.*—Small.
*Color.*—Light purplish pink [249. l.pPk].

FRUIT

Maturity when described: Firm eating ripe, Jul. 3, 1995.
Date of first picking: Jun. 26, 1995.
Date of last picking: Jul. 7, 1995.
Size: Uniform, medium.
*Average diameter axially.*—2 11/16" [68.3 mm. ].
*Average transversely in suture plane.*—2 9/16" [65.1 mm.].
Form: Globose, uniform, symmetrical.
*Longitudinal section form.*—Round.
*Transverse section through diameter.*—Round, slightly compressed.
Suture: An inconspicuous line toward the apex, becomes a shallow groove towrad the base and sharper near the stem, having a slight depression beyond the pistil point,
Ventral surface: Rounded, lipped throughout.
Lips: Slightly unequal.
Cavity: Flaring, circular, suture showing on one side.
*Depth.*—3/8" [9.5 mm.].
*Breadth.*—3/4" [19.1 mm.].
Base: Truncate, but cunneate when viewed along suture plane.
Apex: Rounded to truncate.
Pistil point: Negligible in length, apical with most depressed within the suture.
Stem: Medium.
*Average length.*—3/8" [9.5 mm.].
*Average width.*—3/16" [4.8 mm.].
Skin:
*Thickness.*—Medium.
*Texture.*—Medium.
*Tenacity.*—tenacious to flesh.
*Tendency to crack.*—Slight in the wet season.
*Color.*—Very deep red [14. v.deep R] over a moderate red [15. m.R] background with moderate orange [53. m.O] freckling toward the apex.
Flesh:
*Color.*—Greenish white [153. gWhite] with some having slight moderate red [15. m.R] streaking very near the stone.
*Surface of pit cavity.*—Clingstone.
*Amygdalin.*—Wanting.
*Juice.*—Abundant, rich.
*Texture.*—Firm, tough, crisp.
*Fibers.*—Abundant, fine.
*Ripens.*—Evenly.
*Flavor.*—Subacidic and sweet, with 16 to 18 brix.
*Aroma.*—Moderate.
*Eating quality.*—Best.

STONE

Type: Clingstone.
Form: Oval.
Base: Straight.
Apex: Acute.
Sides: Equal.
Surface: Irregular horizontal furrowing toward the apex and pitted toward the base.
Ridges: Jagged toward the base.
Color: Moderate orange [53. m.O] when first removed, light yellowish brown [76. l.yBr] on the inside.
Pit wall: 1/4" [6.4 mm.]. thick.
Tendency to split: Very slight.
Kernel:
*Form.*—Oval.
*Taste.*—Bitter.
*Viable.*—Yes.
*Average width.*—1/2" [12.7 mm.].
*Average length.*—3/4" [19.1 mm.].
*Skin color.*—Pale yellow [89. p.Y] when first removed.
*Pellicle color.*—Light grayish yellowish brown [79. l.gy.yBr].
*Amygdalin.*—Abundant.

USE

Market: Fresh and long distance shipping.
Keeping quality: Very good.
Shipping quality: Very good.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its pollen parent, the June Pearl (U.S. Plant Pat. No. 9,360), by producing white flesh clingstone nectarines that are subacidic in flavor, medium in size, full red in skin color and virtually free from red texture bleeding, but is distinguished therefrom and an improvement thereon by producing fruit that ripens about two weeks later, that is firmer in texture, that is sweeter in flavor, and that is less prone to a protruding tip at the apex.

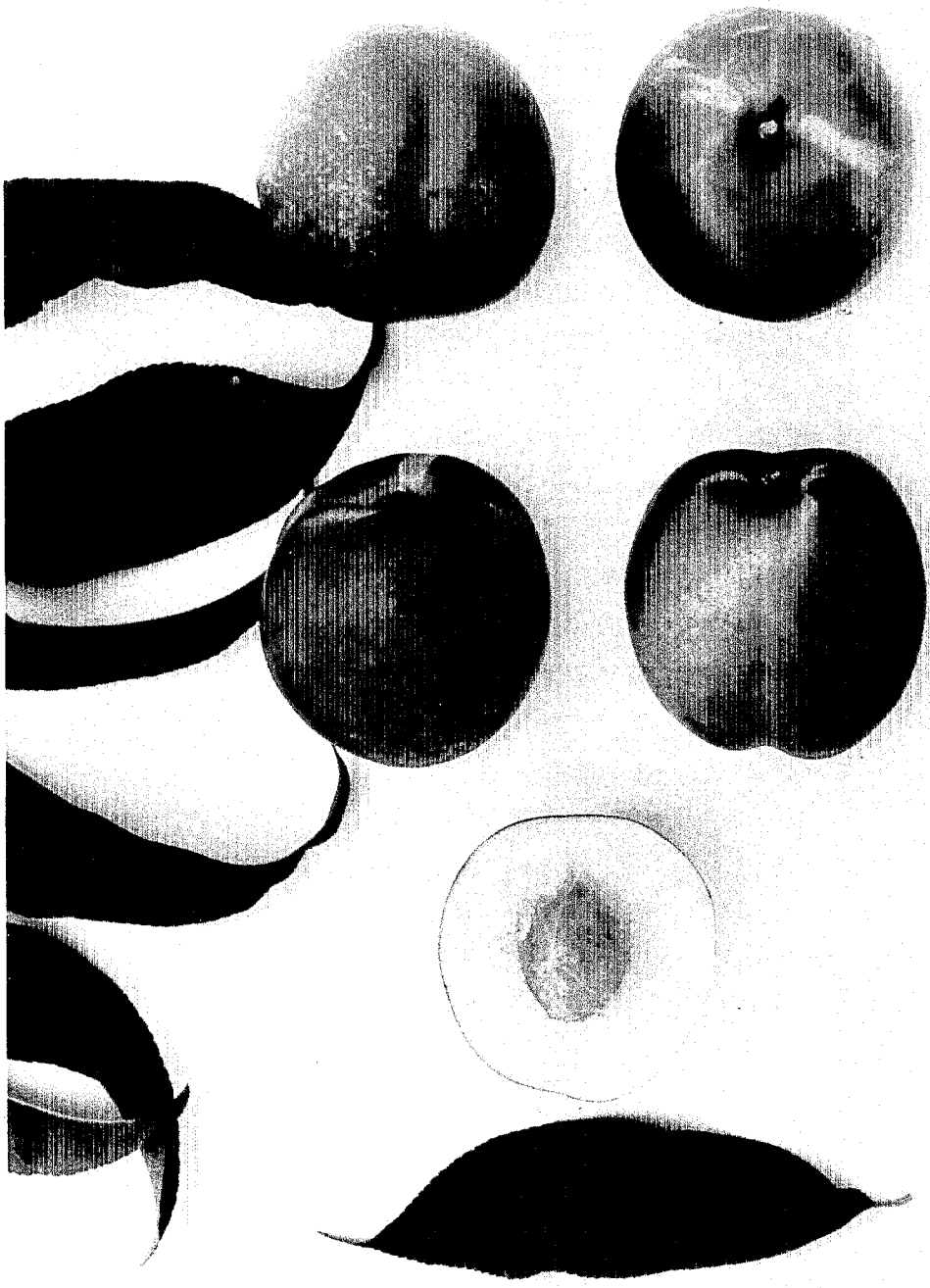

* * * * *